US011033735B2

(12) United States Patent
Hess et al.

(10) Patent No.: US 11,033,735 B2
(45) Date of Patent: Jun. 15, 2021

(54) PACER WIRE MANAGEMENT DEVICES AND METHODS

(71) Applicants: Ian Nolan Hess, Kaysville, UT (US); Cory Denton Smith, Salt Lake City, UT (US); Rami Musa Shorti, South Jordan, UT (US)

(72) Inventors: Ian Nolan Hess, Kaysville, UT (US); Cory Denton Smith, Salt Lake City, UT (US); Rami Musa Shorti, South Jordan, UT (US)

( * ) Notice: Subject to any disclaimer, the term of this patent is extended or adjusted under 35 U.S.C. 154(b) by 360 days.

(21) Appl. No.: 15/892,257

(22) Filed: Feb. 8, 2018

(65) Prior Publication Data

US 2018/0221654 A1 Aug. 9, 2018

Related U.S. Application Data

(60) Provisional application No. 62/456,292, filed on Feb. 8, 2017.

(51) Int. Cl.
*A61N 1/362* (2006.01)
*A61N 1/05* (2006.01)
*A61N 1/04* (2006.01)
*H01R 13/58* (2006.01)
*H01R 13/73* (2006.01)
(Continued)

(52) U.S. Cl.
CPC ............ *A61N 1/0587* (2013.01); *A61N 1/048* (2013.01); *A61N 1/3625* (2013.01); *A61N 1/0492* (2013.01); *A61N 1/0502* (2013.01); *H01R 13/5833* (2013.01); *H01R 13/72* (2013.01); *H01R 13/73* (2013.01); *H01R 31/06* (2013.01); *H01R 2201/12* (2013.01)

(58) Field of Classification Search
CPC .... A61N 1/0587; A61N 1/048; A61N 1/3625; A61N 1/0502; A61N 1/0492; H01R 2201/12; H01R 13/5833; H01R 13/73; H01R 13/72; H01R 31/06
See application file for complete search history.

(56) References Cited

U.S. PATENT DOCUMENTS 3,085,577 A 4/1963 Berman et al.
3,598,128 A 8/1971 Chardack
(Continued)

FOREIGN PATENT DOCUMENTS

WO 2011035189 3/2011

OTHER PUBLICATIONS

Baas, et al., Care and Safety of Pacemaker Electrodes in Intensive Care and Telemetry Nursing Units, American Journal of Critical Care, Jul. 1997, vol. 6, No. 4, pp. 302-311.

*Primary Examiner* — Mallika D Fairchild
(74) *Attorney, Agent, or Firm* — Jason P. Webb; Pearson Butler

(57) ABSTRACT

An epicardial pacer wire management device can include a spool defining a recessed region that encompasses the spool. The recessed region can receive a portion of a pacer wire. The device can further include a connector attached to the spool, and the connector can be electrically coupled with an exposed tip of the pacer wire. The device can further include an electrical port attached to the spool that can communicate with a pacing control unit. The device may include an electrical communication line electrically coupled between the connector and the electrical port.

12 Claims, 16 Drawing Sheets

(51) Int. Cl.
    *H01R 13/72*     (2006.01)
    *H01R 31/06*     (2006.01)

(56) References Cited

U.S. PATENT DOCUMENTS

| | | |
|---|---|---|
| 3,964,490 A | 6/1976 | Nelms |
| 4,266,552 A | 5/1981 | Dutcher |
| 4,276,882 A | 7/1981 | Dickhudt |
| 4,442,840 A | 4/1984 | Wojciechowicz, Jr. |
| 4,466,441 A | 8/1984 | Skubitz et al. |
| 4,693,258 A | 9/1987 | Osypka et al. |
| 5,169,002 A | 12/1992 | Evans et al. |
| 5,241,957 A | 9/1993 | Camps et al. |
| 5,350,419 A | 9/1994 | Bendel et al. |
| 5,427,243 A | 6/1995 | Roshdy |
| 5,456,699 A | 10/1995 | Armstrong |
| 5,871,528 A | 2/1999 | Camps et al. |
| 5,999,835 A | 12/1999 | Osypka |
| 6,021,355 A | 2/2000 | Shchervinsky |
| 6,163,728 A | 12/2000 | Wildon |
| 6,192,278 B1 | 2/2001 | Werner et al. |
| 6,205,355 B1 | 3/2001 | Lomanto et al. |
| 6,254,425 B1 | 7/2001 | Shchervinsky et al. |
| 6,318,374 B1 | 11/2001 | Burger |
| 6,327,507 B1 | 12/2001 | Buchan |
| 6,397,108 B1 | 5/2002 | Camps et al. |
| 6,466,824 B1 | 10/2002 | Struble |
| 6,533,216 B1 * | 3/2003 | Bumgarner ............ B65H 75/14 242/118.41 |
| 6,644,998 B2 | 11/2003 | Kaufmann et al. |
| 6,671,534 B2 | 12/2003 | Putz |
| 7,032,854 B2 | 4/2006 | Marsden |
| 7,106,301 B2 | 9/2006 | Smith et al. |
| 7,130,699 B2 | 10/2006 | Huff et al. |
| 7,204,703 B1 | 4/2007 | Hendrixson |
| 7,302,299 B2 | 11/2007 | Wojciechowicz |
| 7,454,251 B2 | 11/2008 | Rezai et al. |
| 7,769,443 B2 | 8/2010 | Barolat |
| 7,777,140 B2 | 8/2010 | Cappa et al. |
| 8,209,016 B2 | 6/2012 | Deininger et al. |
| 8,571,627 B2 | 10/2013 | Tremblay et al. |
| 8,666,510 B2 | 3/2014 | Chinn et al. |
| 8,843,200 B2 | 9/2014 | Mehdizadeh et al. |
| 9,014,817 B2 | 4/2015 | Kolberg et al. |
| 9,320,891 B2 | 4/2016 | Anderson et al. |
| 9,439,599 B2 | 9/2016 | Thompson et al. |
| 2003/0040784 A1 | 2/2003 | Pasternak et al. |
| 2003/0120327 A1 * | 6/2003 | Tobritzhofer ............ A61N 1/05 607/116 |
| 2004/0149533 A1 | 8/2004 | Milano |
| 2005/0075707 A1 | 4/2005 | Meadows et al. |
| 2006/0271136 A1 | 11/2006 | Wojciechowicz |
| 2007/0027388 A1 | 2/2007 | Chou |
| 2008/0139953 A1 | 6/2008 | Baker et al. |
| 2008/0177168 A1 * | 7/2008 | Callahan ............ A61B 5/04085 600/382 |
| 2011/0207352 A1 | 8/2011 | Camps et al. |
| 2011/0257503 A1 | 10/2011 | Mehdizadeh et al. |
| 2011/0270100 A1 * | 11/2011 | Chang ............... A61B 5/04085 600/509 |
| 2017/0080236 A1 | 3/2017 | Karl et al. |

* cited by examiner

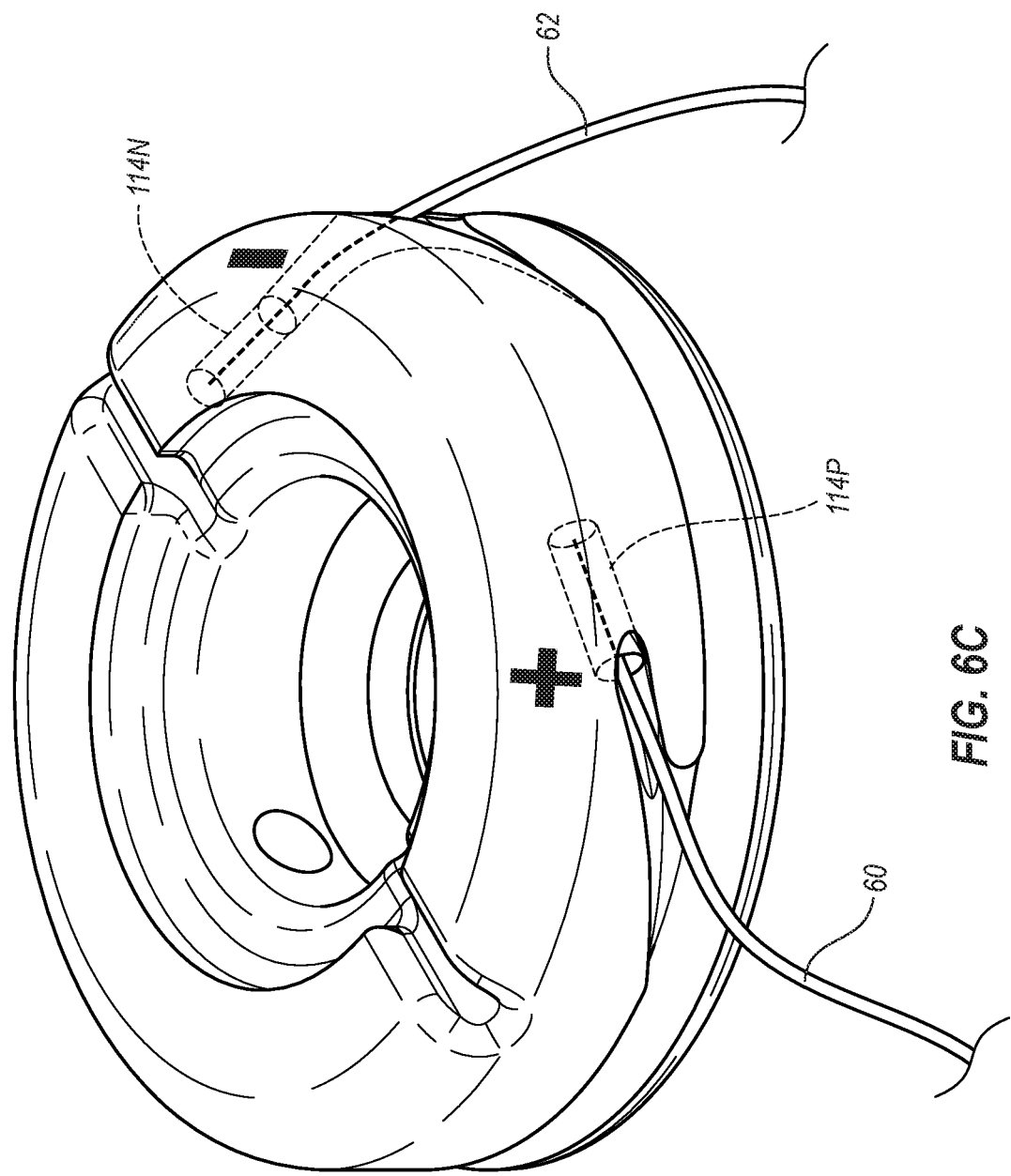

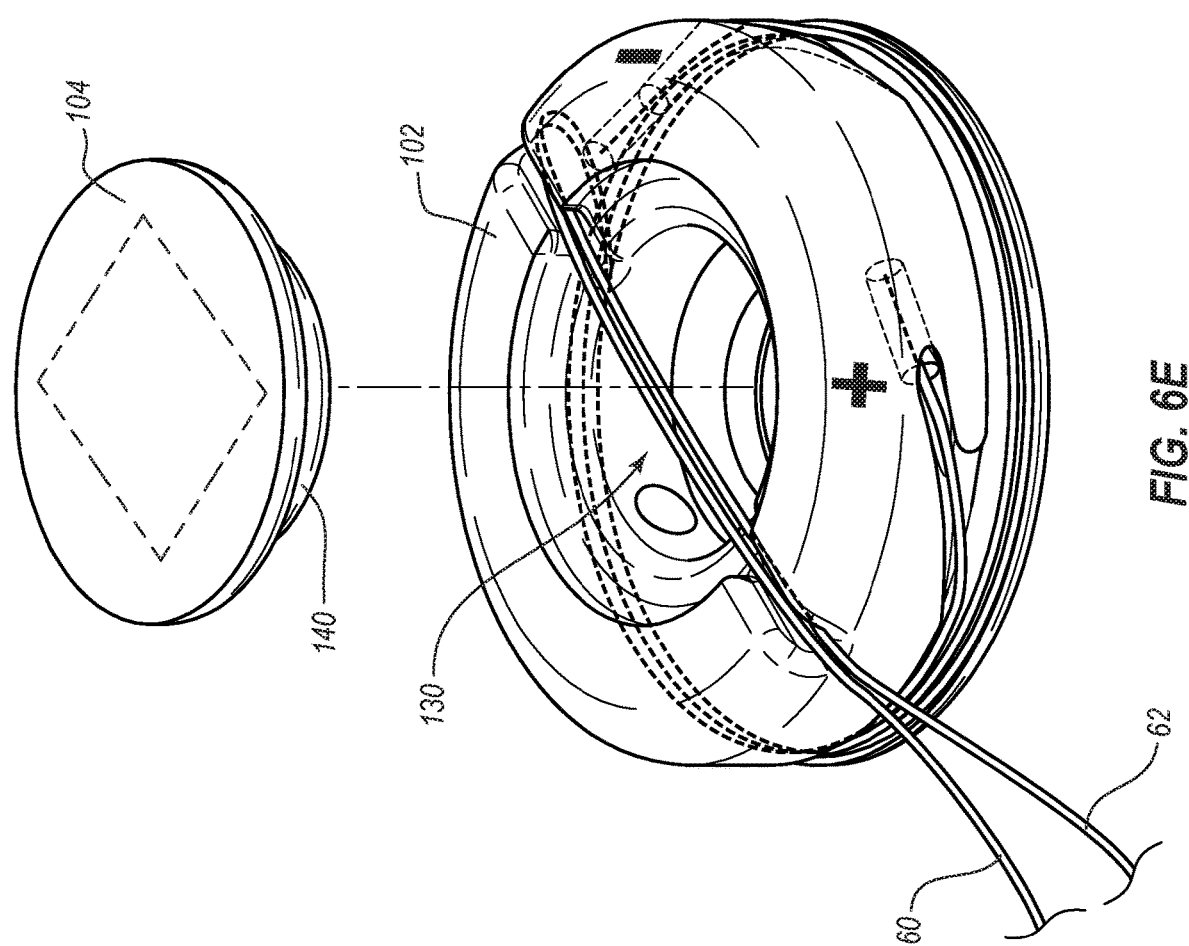

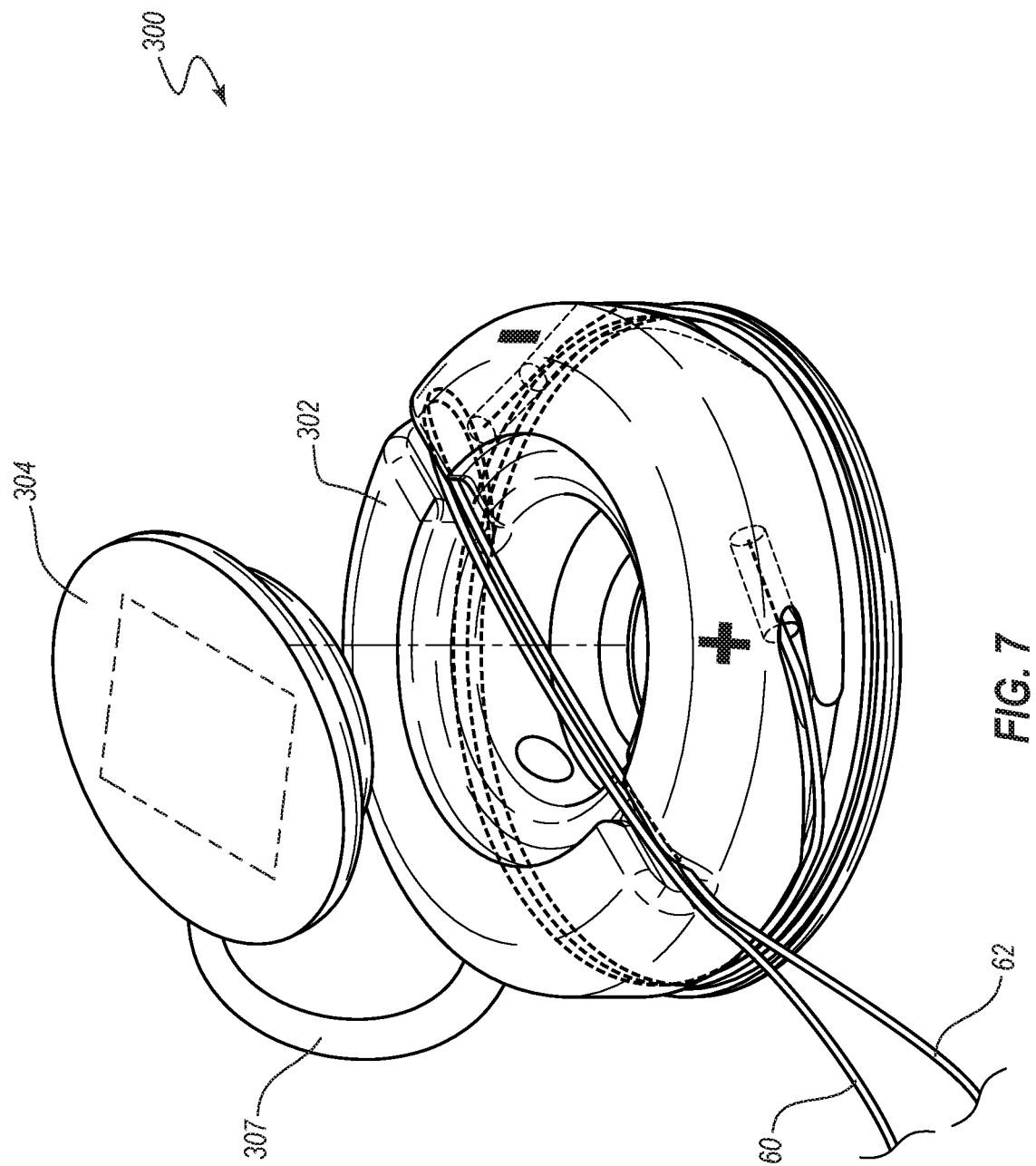

PACER WIRE MANAGEMENT DEVICES AND METHODS

RELATED APPLICATIONS

This application claims priority to U.S. Provisional Application No. 62/456,292, filed on Feb. 8, 2017 and titled "Pacer Wire Management Devices and Methods," which is incorporated herein by reference in its entirety.

BACKGROUND

The present disclosure relates to epicardial pacer wires, and relates more particularly to devices and methods for managing epicardial pacer wires.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIGS. 6A-6H are perspective views of various stages of an illustrative method of using a pacer wire management device, with FIG. 6H further including a cross-sectional view such as that depicted in FIG. 4;

FIG. 7 is a perspective view of another embodiment of a pacer wire management device;

DETAILED DESCRIPTION

Figure 1:
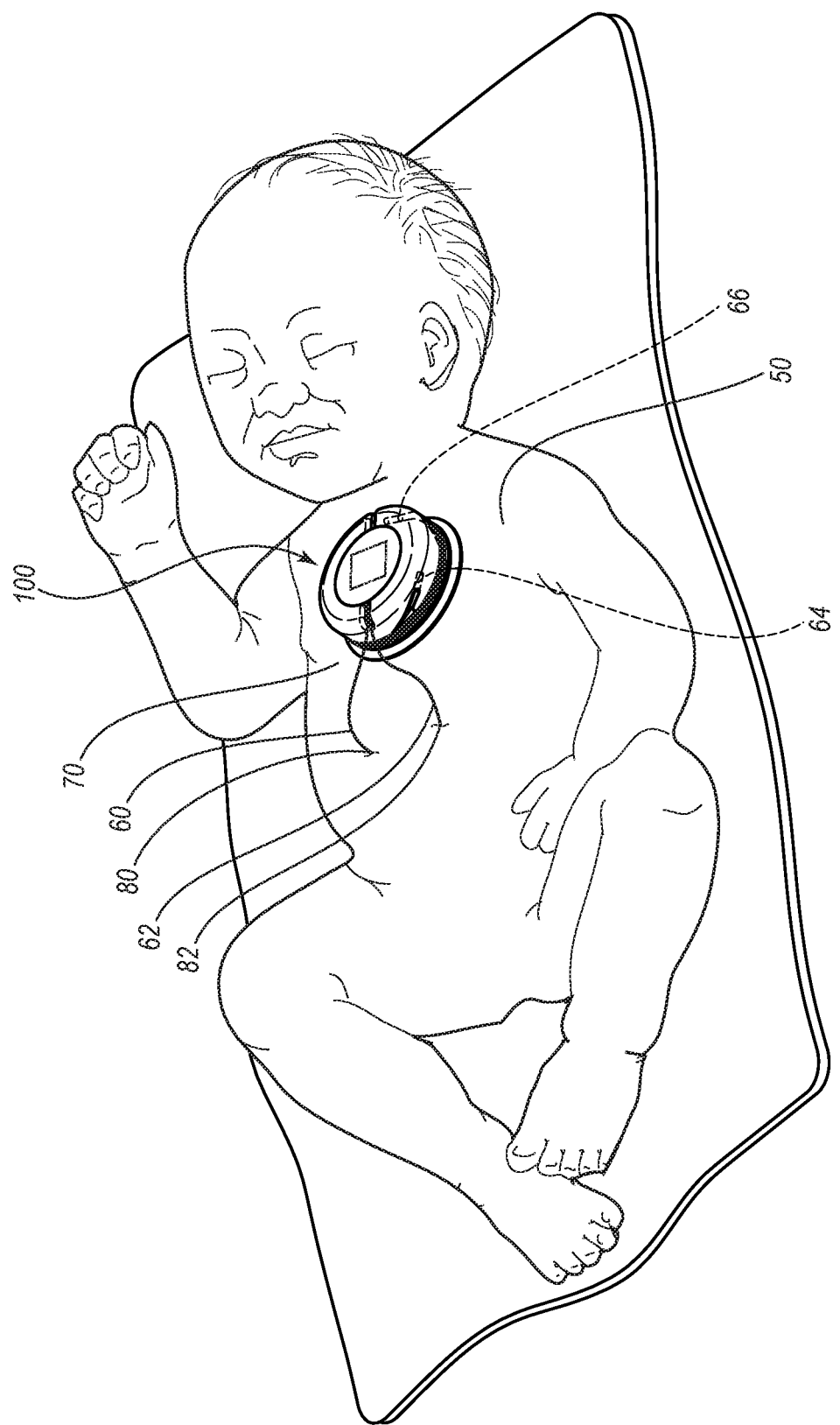
FIG. 1 is a perspective view of an embodiment of a pacer wire management device in use with a patient.

Numerous devices have been proposed and implemented for delivering electric pulses to the heart. One commonly used device is the epicardial pacemaker. Epicardial pacer wires are pacemaker leads usually made of Teflon™ insulated stainless steel and are inserted into the epicardial surface of the heart during coronary artery bypass surgery. These wires are sutured to the atrium and/or ventricle of the heart by the surgeon and then brought through the subcutaneous tissue of the chest wall. A skin wire or lead may also be used.

Typically, epicardial pacer wires extend outwardly through the chest of the patient (e.g., six to twelve inches) and end in a stiff, uninsulated tip. This tip is used for insertion into ventricular and/or atrial ports of a temporary pacemaker. This pacemaker may be used, for example, in the case of heart dysrhythmias. Through these epicardial pacer wires, the temporary pacemaker delivers an electrical charge that stimulates an electrical response in the heart, causing a heartbeat. This temporary cardiac pacing has proven to be a significant lifesaving technique for post-operative cardiac patients.

Pacer wires generally come in pairs and run from their insertion site in either the ventricles or atria, and out through the skin. Some patients only have one set of wires—either ventricular or atrial. Other patients may have both sets of wires. The atrial wires are on the right side of the patient and the ventricular wires are on the left side of the patient. As previously noted, the wires are used to pace a patient's heart during emergencies that may arise after open-heart surgery during the period that the heart is recovering from the shock of cardiac bypass and the trauma of surgery.

Known devices and methods for managing pacer wires suffer from a variety of drawbacks. Pacer wire management can include storage and/or protection of the pacer wires during periods between use. Pacer wire management also includes that manner in which the wires are used for pacing.

Devices and methods for storing pacer wires often involve items that are designed or intended for other uses and lack consistency in application. For example, pacer wires are wrapped around such disparate items as tongue depressors, syringe barrels, glass or plastic lab tubes, or needle caps. In other instances, a finger cot or a torn-off finger of a latex/nitrile glove is used to store the pacer wires. In still other instances, the pacer wires are wound and taped directly to the skin of the patient (e.g., taped to the abdomen) using Tegaderm™ or other form of tape.

Many of the disadvantages of such storage methods are evident from just one of the foregoing examples: the use of lab tubes (e.g., glass tubes or plastic microtainers). Storing pacer wires in lab tubes is one of the more common approaches. For the best possible outcome using this method, each individual wire should be stored in a separate tube, the tube should be devoid of any gel, and lids should not be placed on the tubes when the wires are stored therein. Separate tubes are used to reduce the chances of forming a closed circuit by contacting the pacer wire tips. Gel-containing tubes should be avoided because the leads could become coated in the gel. If this happens, the gel may form an insulating barrier on the leads that can prevent the leads from conducing electricity from the pacer control unit (also referred to herein as a "pacer box," "pacing unit," or "pacing control unit"), or stated otherwise, can prevent the leads from functioning properly. This error is one that is easily made and one that may not be immediately apparent to the practitioner. Lids should not be placed on the tubes as this can create stress points on the frail wires and can result in broken wires. Pacer wires are fragile, and once a wire breaks, the entire circuit is compromised. Although it is possible to pace with only one good wire, the method for doing so is time-consuming, cumbersome, and painful to the patient. In particular, a skin lead that is embedded into the skin of the patient is used. Moreover, if the patient is in a slow (bradycardia) rhythm, there may not be sufficient time for placement of a skin lead, and thus CPR or transcutaneous pacing may be used instead. These alternative approaches have drawbacks such as extreme discomfort to the patient and the potential for further injury to the patient.

Despite the negative results for doing so, practitioners do not always adhere to, or may not be aware of, the foregoing precautions when using lab tubes. For example, it is not uncommon for practitioners to place multiple leads in the same tube, to use lids with tubes into which a pacer wire has been inserted, and/or to use gel-containing tubes to store pacer wires.

Another significant risk associated with current storage mechanisms is microshock, which is the transmission of undesirable electricity through the wires and to the heart, which can potentially cause fatal arrhythmias. For example, minute electric charges can be delivered to the heart through the epicardial wires; although such charges are usually not felt by the patient, they can cause lethal ectopy. Sources of minute electric charges can include static electricity or ungrounded, unchecked electrical equipment, such as a hospital bed frame. Typically, the pacer wires are stored together in the same glass tube or finger cot, or they are both taped together underneath a clear occlusive dressing. When the pacer wires are stored together in such manners, the conductive tips of the leads are often in contact, thus creating a circuit that drastically increases the chances of microshock.

Moreover, when both wires are removed from the storage device, one wire is typically coupled to the pacer box cable while the other is left dangling and potentially contacting a variety of surfaces, thus increasing the chances of errant electricity being applied to the heart. This is an example of another form of pacer wire management—namely, the use of pacer wires during a pacing event—that suffers drawbacks under present approaches.

A further drawback of present methodologies includes the delays they introduce to using the pacer wires. For example, known storage methods usually require unraveling and/or untangling of the wires prior to use. Moreover, the practitioner must ensure that the leads are coupled to the proper polarity interfaces of the pacer box cable, and further, that the pacer box cable is connected to the proper port of the pacer box (i.e., the atrial or ventricle port). Not only can this process be time-consuming, it also presents the risk of set-up error. Wires from the atria and wires from the ventricles can be difficult to distinguish from each other with all of the dressings, cables, wires, and other equipment present on a patient. The wires may be labeled, but these labels sometimes fall off. This creates potential for the wires to be placed incorrectly into the pacer during an emergency, when time is of the utmost importance.

Another potential for set-up error involves situations where a skin lead is used for pacing. In such circumstances, the pacer wire leads must be inserted into the pacer box cable correctly or the heart will not be paced. The skin lead must be inserted into the positive (+) slot on the cable and the heart lead must be inserted into the negative (−) slot on the cable. During an emergency, it is easy to make a mistake and/or have difficulty properly inserting the leads into the proper channels of the pacer box cable (i.e., into the designated positive (+) or negative (−) channel of a connection adapter at a proximal end of the cable)—which can require significant dexterity and fine motor skills even under calm circumstances—due to, for example, adrenaline, commotion, distractions, etc.

Embodiments disclosed herein ameliorate or remedy one or more of the foregoing drawbacks of known pacer wire management. For example, various embodiments provide a standardized method for storing pacer wires, provide heightened protection against microshock, protect pacer wires from excess bending during storage and/or eliminate stress points in the wires during storage, provide a simplified mechanism for electrically coupling the pacer wires to a pacer box, and/or provide a system for clearly distinguishing the positive pacer wire from the negative pacer wire for ready transfer of the pacer wires from the management device to the pacer box cable in instances where a traditional pacer box cable is used. One or more of these and/or other or further advantages of embodiments discussed herein will be apparent from the present disclosure.

FIG. 1 is a perspective view of an embodiment of a pacer wire management device 100 in use with a patient 50. The patient 50 is depicted as an infant. Although the device 100 is advantageously used in the post-operative context of pediatric congenital heart disease surgeries, it should be understood that the device 100 is advantageous in further contexts, including for use with adults.

The patient 50 has been provided with epicardial pacer wires 60, 62. Each pacer wire 60, 62 is attached to the heart of the patient 50 at a distal end thereof. The pacer wires 60, 62 extend through insertion/exit sites 80, 82 in the skin 70, and the proximal portions of the pacer wires 60, 62 are disposed at an exterior of the patient 50. The device 100 can be configured to store a majority, or substantially all, of these proximal portions of the pacer wires 60, 62, including proximal ends 64, 66 thereof.

As shown in the illustrated embodiment, the device 100 can be fixedly secured or otherwise coupled to the skin 70 of the patient 50. In particular, in the illustrated arrangement, the device 100 is attached to the skin 70 of the chest of the patient 50. The device 100 can also be coupled to the skin 70 at other locations, such as on the belly of the patient 50. In FIG. 1, the patient 50 includes only one set of pacer wires 60, 62, which in the illustrated arrangement, are atrial wires. In other instances, a patient 50 may only have one set of wires that are ventricular wires. In still other instances, a patient 50 may have a set of ventricular wires and a separate set of atrial wires. In some of such instances, two pacer wire management devices can be used. In still further instances, a patient 50 may only have one transcutaneous wire for one or more of the atrial or ventricular regions. A skin wire or lead can also be used, and can be stored on the device analogous to pacer wires 60, 62.

Figure 2:
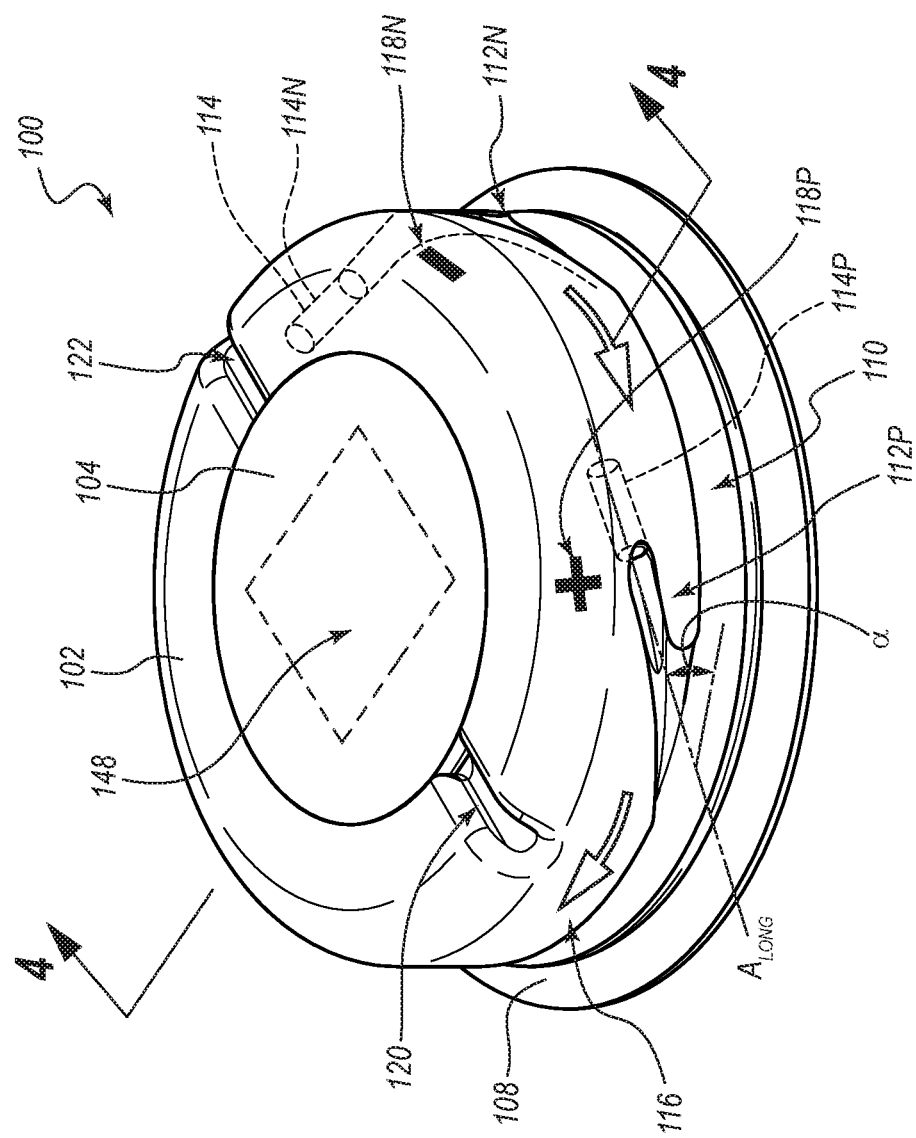
FIG. 2 is a perspective view of the pacer wire management device of FIG. 1.
Figure 3:
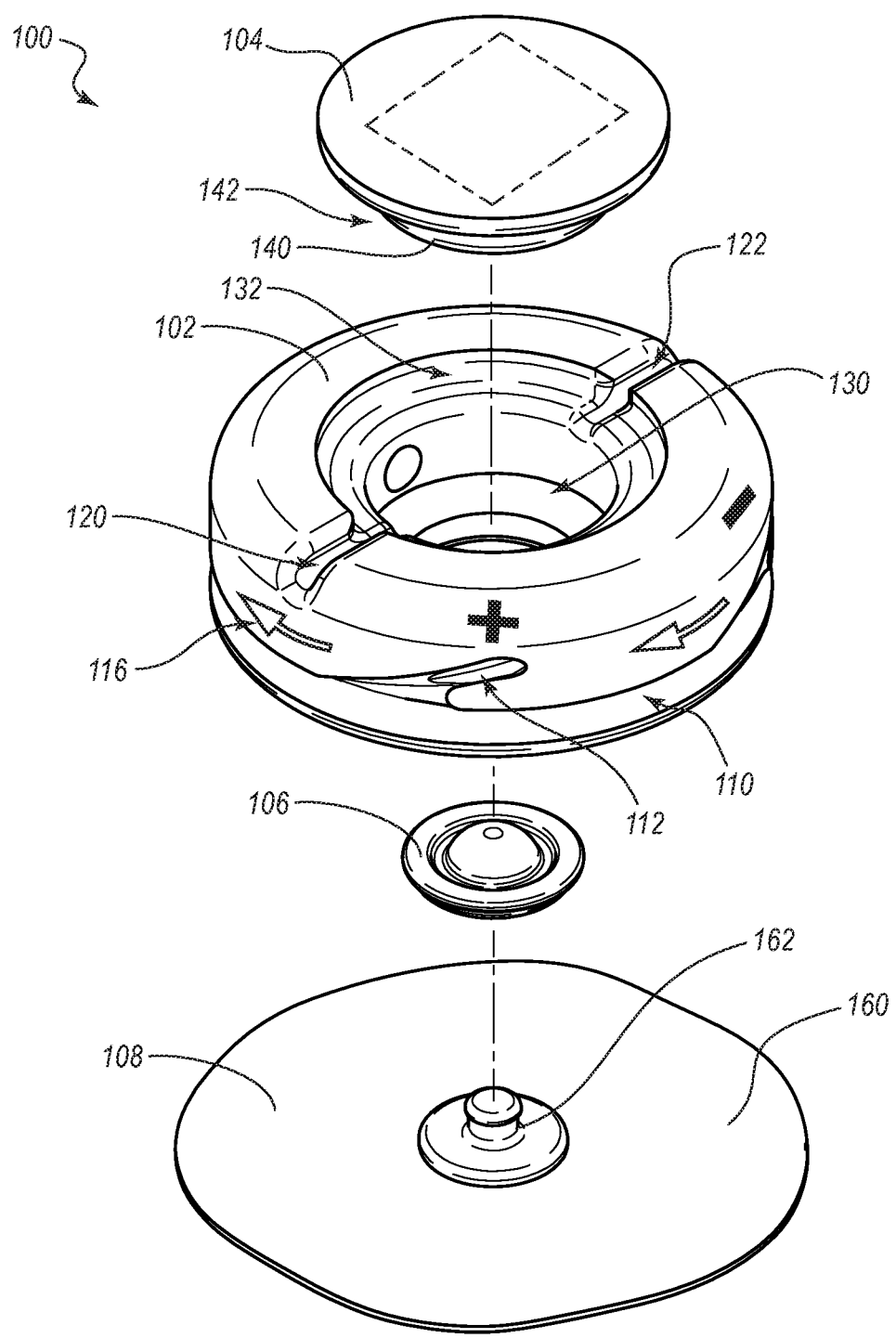
FIG. 3 is an exploded perspective view of the pacer wire management device of FIG. 1.
Figure 4:
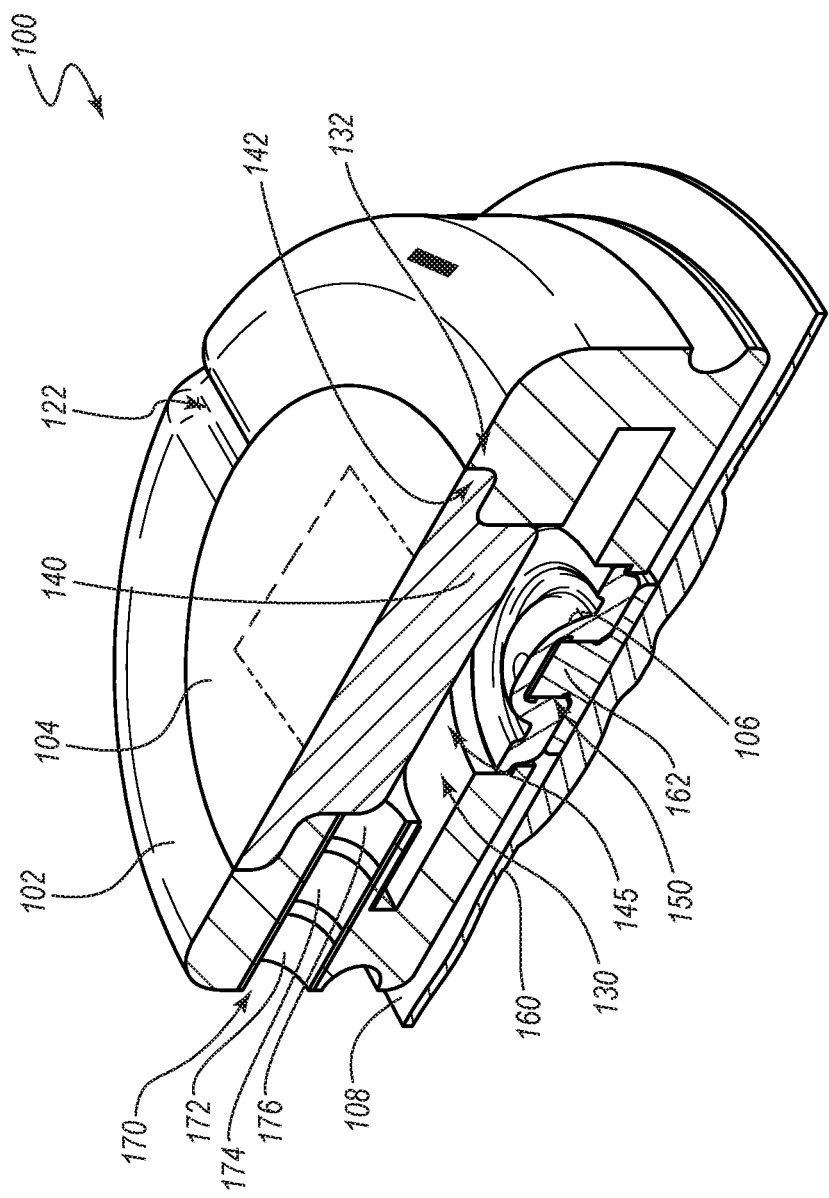
FIG. 4 is a cross-sectional perspective view of the pacer wire management device, the cross-section having been taken along the view line 4-4 in FIG. 2.

FIGS. 2-4 depict various views of the device 100. The device 100 can include a spool 102 about which the pacer wires 60, 62 can be wound. In the illustrated embodiment, the device 100 further includes a cap 104 that can secure the pacer wires 60, 62 to the spool 102. As further discussed below, in some embodiments, the cap 104 can be selectively attachable to and detachable from the spool 102. In some embodiments, the device 100 includes a connector 106 via which the device 100 can be selectively attached to or detached from a mounting pad 108.

In some embodiments, the spool 102 can be substantially disk-shaped. In certain embodiments, the shape of the spool 102 can be defined in relation to the perimeter of a channel or groove 110 that extends around the spool 102. For example, as shown in the illustrated embodiment, the spool 102 can be described as being is substantially round and/or circular. In other embodiments, the shape of the spool 102 (or the shape of a channel or groove 110) can be substantially oval. Other shapes and configurations are also contemplated.

The spool 102 can define an indentation, channel, or groove 110 into which the pacer wires 60, 62 are received. In the illustrated embodiment, the groove 110 is formed as a recess that extends radially inward relative to an outer surface of the spool 102. The groove 110 extends around a full perimeter (e.g., circumference, in the illustrated embodiment) of the spool 102. In the illustrated embodiment, the groove 110 is positioned at a base end of the spool 102. A depth (i.e., radial dimension) and/or height (i.e., longitudinal dimension) of the groove 110 can be sufficiently large to ensure that those portions of the pacer wires 60, 62 that are wrapped about the spool 102 are recessed from the outer surface of the spool 102. Such an arrangement may inhibit inadvertent snagging of the wrapped portion of the pacer wires 60, 62.

In certain embodiments, the spool 102 can further define one or more grooves or channels 112 (also depicted as 112P, 112N) that extend from the groove 110. A connector 114 (also depicted as 114P, 114N) can also be positioned at an end of each channel 112 that is opposite from the groove 110. In some embodiments, the connector 114 comprises an electrical connector 114. In particular embodiments, an electrical connector 114P, 114N can be positioned at an end of each channel 112P, 112N, respectively, that is opposite from the groove 110. The electrical connectors 114P, 114N may also be referred to as terminals 114P, 114N. In some embodiments, the connectors 114P, 114N are embedded in the spool 102. Stated otherwise, a material of which the spool 102 is formed can encompass the connectors 114P, 114N. In some embodiments, the spool 102 comprises an insulating or dielectric material, and thus the connectors 114P, 114N can be shielded from an environment around the spool 102. The channel 112P and the connector 114P can be configured for coupling with a positive pacer wire 60, while the channel 112N and the connector 114N can be configured for coupling with a negative pacer wire 62. In some embodiments, the connectors 114P, 114N can be configured to protect the exposed tips of the pacer wires 60, 62, such as by inhibiting contact with moisture. For example, in some embodiments, the connectors 114P, 114N can be configured to operate in manners such as or similar to grease plugs. The connectors 114P, 114N can be configured to both physically and electrically couple with the exposed tips of the pacer wires 60, 62. In other embodiments, the connectors 114P, 114N are only configured to physically couple the exposed tips of the pacer wires 60, 62.

In the illustrated embodiment, the connector 114P and the channel 112P define a longitudinal axis $A_{LONG}$ that is disposed at an angle $\alpha$ relative to a plane (not shown) that extends through a full perimeter of the groove 110. Stated otherwise, longitudinal axis $A_{LONG}$ defined by the connector 114P and the channel 112P is disposed at an angle $\alpha$ relative to a plane (not shown) that is transverse to an axis of rotation about which the pacer wire 60 is wound around the spool 102. The angle $\alpha$ and/or a length or other configuration of the channel 112P can provide a smooth transition from the connector 114P to the groove 110. Stated otherwise, the channel 112P, including the angle $\alpha$ at which it and/or the connector 114P are oriented relative to the groove 110, can avoid sharp bends, sharp transitions, or kinks that might otherwise undesirably bend and/or weaken the pacer wire 60. The angle $\alpha$ can be acute. In various embodiments, the angle $\alpha$ is no greater than 30, 45, or 60 degrees. In the illustrated embodiment, the channel 112P is flared at a base end thereof, which is opposite from the connector 114P, which can also assist in providing a smooth transition to the groove 110 and avoid bending the pacer wire 60.

The connector 114N and/or the channel 112N can be configured the same as or similar to the connector 114P and/or the channel 112P. For example, one or more of the connector 114N and the channel 112N can define a longitudinal axis $A_{LONG}$ that is disposed at an angle $\alpha$, in manners such as just described. The angle $\alpha$ may either be the same as or different than the angle $\alpha$ for the connector 114P and/or the channel 112P.

In some embodiments, an acute angle $\alpha$ points in a desired wrapping direction. For example, in the illustrated embodiment, it can be desirable to wrap the pacer wire 60 in a direction that is clockwise relative to the device 100 in the orientation depicted in FIGS. 2-4. This wrapping direction can be preferred, as it can avoid the formation of sharp bends in the pacer wire 60. Similarly, the pacer wire 60 would be unwrapped in a counterclockwise direction. In FIG. 2, the angle $\alpha$ points in the clockwise direction. In some embodiments, one or more indicia 116 are provided on the spool 102 to indicate the preferred direction of wrapping. The indicia 116 may include an arrow and/or text specifying the preferred wrapping direction.

In the illustrated embodiment, the connectors 114P, 114N and the channels 112P, 112N are angularly spaced from each other by approximately 90 degrees. Other angular spacing is also possible. For example, in various embodiments, the angular spacing is within a range of from about 60 degrees to about 120 degrees, or within a range of from about 45 degrees to about 315 degrees, from about 60 degrees to about 300 degrees, from about 90 degrees to about 270 degrees, or from about 120 degrees to about 240 degrees. In some instances, a relatively large angular spacing can assist in distinguishing the positive terminal 114P from the negative terminal 114N and avoiding practitioner confusion at either the time of coupling or decoupling the pacer wires 60, 62 to or from the device 100. In some embodiments, one or more indicia 118P, 118N are provided on the spool 102 to distinguish the positive terminal 114P from the negative terminal 114N. The indicia 118P, 118N may include an appropriate symbol (e.g., "+", "−") and/or text specifying the polarity of the terminal 114P, 114N. One or more portions of the pacer wires 60, 62 can also be marked or otherwise labeled to distinguish the pacer wire 60 that is to be coupled to the positive terminal 114P and the pacer wire 62 that is to be coupled to the negative terminal 114N. For example, the proximal portion of the pacer wires 60, 62 can be colored differently (e.g., red and black, etc.) to distinguish the pacer wires 60, 62 from one another.

With continued reference to FIGS. 2-4, the spool 102 can include a pair of channels or notches 120, 122 at an upper surface thereof. In particular, the notches 120, 122 can be regions that are recessed downwardly from the upper surface of the spool 102. The notches 120, 122 can be positioned at diametrically opposite sides of the spool 102. As further discussed below, the pacer wires 60, 62 can be positioned within the notches 120, 122. A depth and/or width of the groove in each notch 120, 122 can be sufficiently large to ensure that those portions of the pacer wires 60, 62 that are received within the notches 120, 122 are recessed from the upper surface of the spool 102. Such an arrangement may inhibit inadvertent snagging of the pacer wires 60, 62 at the upper end of the spool 102. In further embodiments, one or more additional pairs of diametrically opposed notches 120, 122 may be present at the upper end of the spool 102, which can provide a user with an additional degree of flexibility in determining how tightly to wind the pacer wires 60, 62 and/or where to position the device 100 on the body of the patient 50. The notches 120, 122 can increase in depth in a radially inward direction. Such a configuration can assist in avoiding pinching or kinking of the pacer wires 60, 62 when the cap 104 is secured to the spool 102.

With reference to FIGS. 3 and 4, the spool 102 can also define a recess or a cavity 130 at interior ends of the notches 120, 122. For example, a recess or cavity 130 can be disposed at a central region of the spool 102. The spool 102 can also define a connection interface 132.

In some embodiments, the cap 104 can define a protrusion 140 that is sized to be received within the recess or cavity 130 of the spool 102. The cap 104 can also define a connection interface 142 that is configured to cooperate with the connection interface 132 to secure the cap 104 to the spool 102. When coupled, the cap 104 and the spool 102 can cooperate to define an enclosure or chamber 145 (see FIG. 4) into which a portion of the pacer wires 60, 62 can be received (see FIGS. 6D-6F). Coupling the cap 104 to the spool 102, such as in the manner depicted in FIGS. 6D-6F (and described further below), can retain the pacer wires 60, 62 in a wound state.

In some embodiments, an outer surface of an upper portion of the cap 104 and or the protrusion 140 can define the connection interface 142. A complementary portion of the spool 102 can define the connection interface 132. In some embodiments, the connection formed by the interfaces 132, 142 is sufficiently strong to keep the cap 104 and the spool 102 in a coupled state under typical forces that may be encountered by the pacer wires 60, 62, such as inadvertent brushing against clothing, etc. In some embodiments, the connection is sufficiently weak to permit the cap 104 to disengage from the spool 102 in situations of greater strain, such as significant snagging. For example, an excessive pull on the pacer wires 60, 62 can cause the cap 104 to pop off of, or otherwise disengage from, the spool 102, and the wound portion of the pacer wires 60, 62 may unravel from around the spool 102, thus serving as a strain relief mechanism that may, for example, inhibit inadvertent extraction of the pacer wires 60, 62 from the patient 50. In various embodiments, the connection interfaces 132, 142 can provide a friction-fit, snap-fit, or other releasable engagement. In other or further embodiments, the connection interfaces 132, 142 may define complementary threading, a detent mechanism, or other suitable engagement mechanism.

With reference again to FIG. 2, the cap 104 can include any suitable indicia 148 indicating the type of wires housed by the device 100. For example, the indicia 148 may include text, such as a letter "A" or "V," to indicate that the device 100 is being used to store either atrial or ventricular leads. In other or further embodiments, the cap 104 may be colored to so indicate. For example, a blue cap 104 may be used for atrial leads, whereas a white cap 104 may be used for ventricular leads. In yet other or further embodiments, the spool 102 may be colored (e.g., blue or white) or otherwise marked to indicate the type of leads that it stores.

Figure 8A:
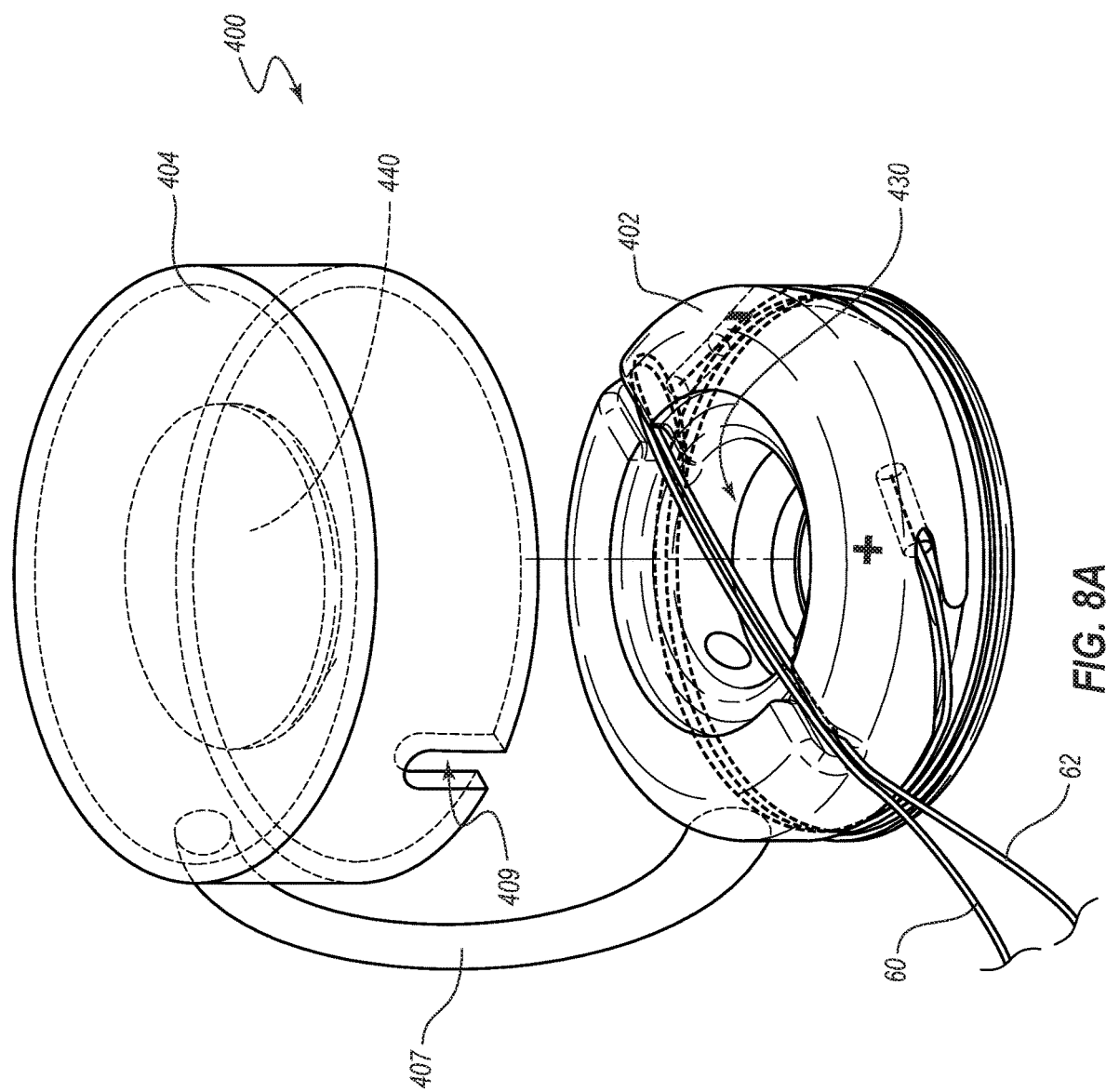
FIGS. 8A and 8B are perspective views of another embodiment of a pacer wire management device.
Figure 8B:
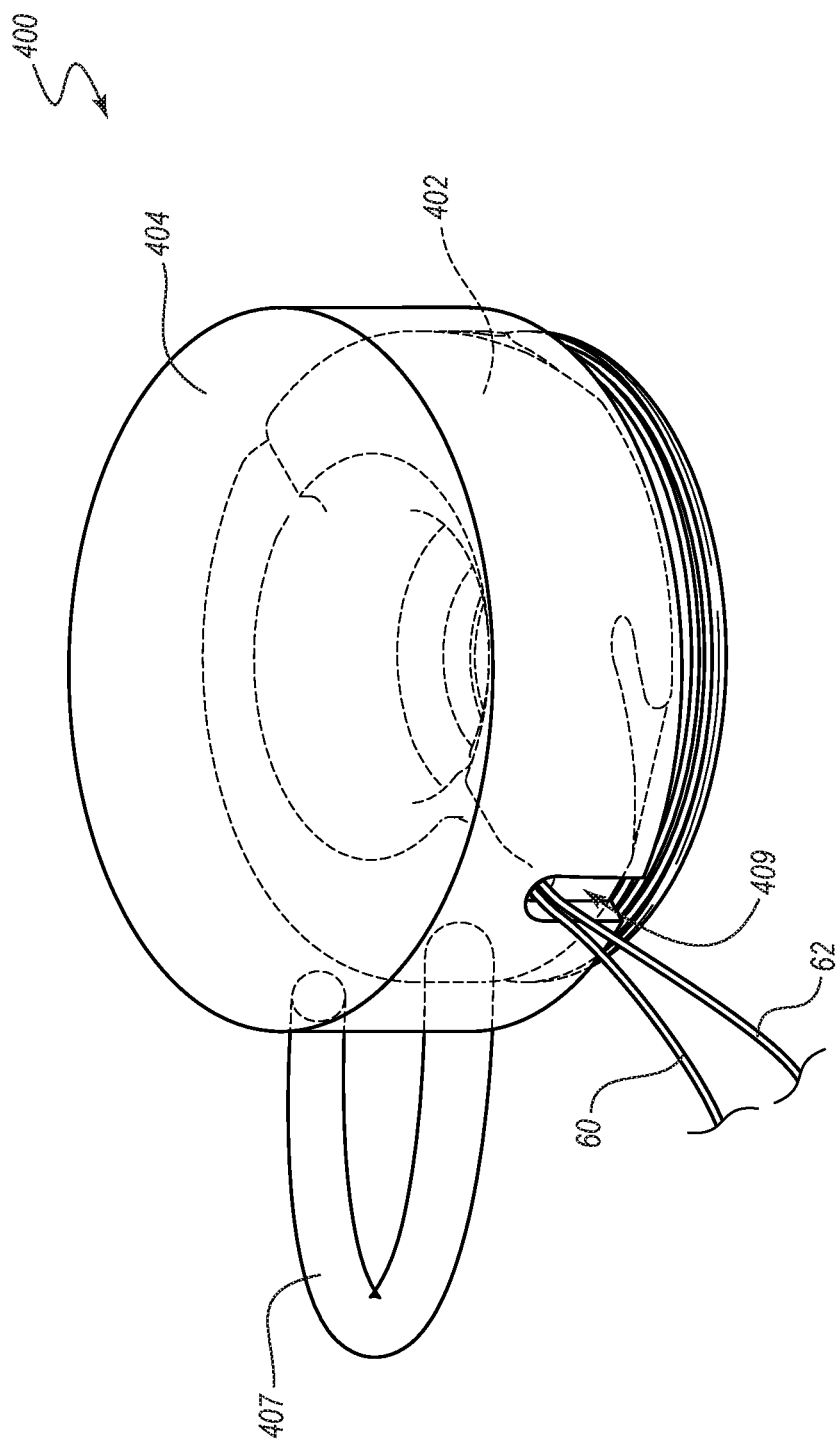

As further detailed below, various types of caps 104 can be used. For example, in some embodiments, a cap 104 can be coupled or tethered to the spool 102 such that the cap 104 remains coupled to the spool 102 when the connection interfaces 132, 142 are disengaged (as is shown in FIG. 7). In still further embodiments, a cover or cap 104 can be configured to be disposed over the spool 102, as is shown in FIGS. 8A and 8B. Other types of caps 104 can also be used.

With reference to FIG. 4, the device 100 can include a connector 106 for coupling the spool 102 to a mounting pad 108. In some embodiments, the connector 106 can be fixedly secured to the spool 102. And in particular embodiments, the connector 106 is integral with the spool 102. The connector 106 can define a connection interface 150 for coupling to a complimentary connector 162 of a mounting pad 108. In some embodiments, the connection interface 150 permits selective coupling and decoupling. For example, a standard snap-fit engagement may be used. The device 100 thus may be connected to the skin of the patient 50 via a mounting pad 108.

In some embodiments, the connector 106 can include or be formed as an electrical connector to electrically communicate with a mounting pad 108 via the connector 162. In particular embodiments, the connector 106 can be configured to electrically and/or physically couple the device 100 to the mounting pad 108.

The mounting pad 108 may be of any suitable variety. For example, in some embodiments, the mounting pad 108 includes a flexible substrate 160 that can be secured to the skin of a patient via a suitable gel or adhesive. In certain embodiments, the mounting pad 108 comprises an electrode pad. Various types of electrode pads can be used, including those presently marketed and those that may be developed in the future. In some embodiments, the mounting pad 108 comprises an EKG pad. In other embodiments, an electrode pad may be incorporated into the device 100. For example, the connectors 106, 162 may instead be formed as a unitary electrical contact, and the substrate 160 and/or adhesive may be positioned at the bottom end of the device 100.

As previously discussed, in some instances, the mounting pad 108 comprises an electrode pad that can be used to deliver electrical signals to the heart via one of the leads (i.e., the positive lead 60), such as where only one pacer wire 60, 62 is attached at the heart of the patient 50. For example, a mounting pad 108 comprising an electrode pad can be used in the place of current skin leads, which are generally implanted in the skin 70 of the patient 50. The practitioner may thus place a mounting pad 108 comprising an electrode pad at a suitable region on the patient 50 in order to achieve this end. A mounting pad 108 comprising an electrode pad can also be used as a backup for one or more skin leads. In some of such instances, the mounting pad 108 can be activated if the one or more skin leads fail. In still further embodiments, a mounting pad 108 comprising an electrode pad can be used in addition to one or more skin leads.

Figure 5A:
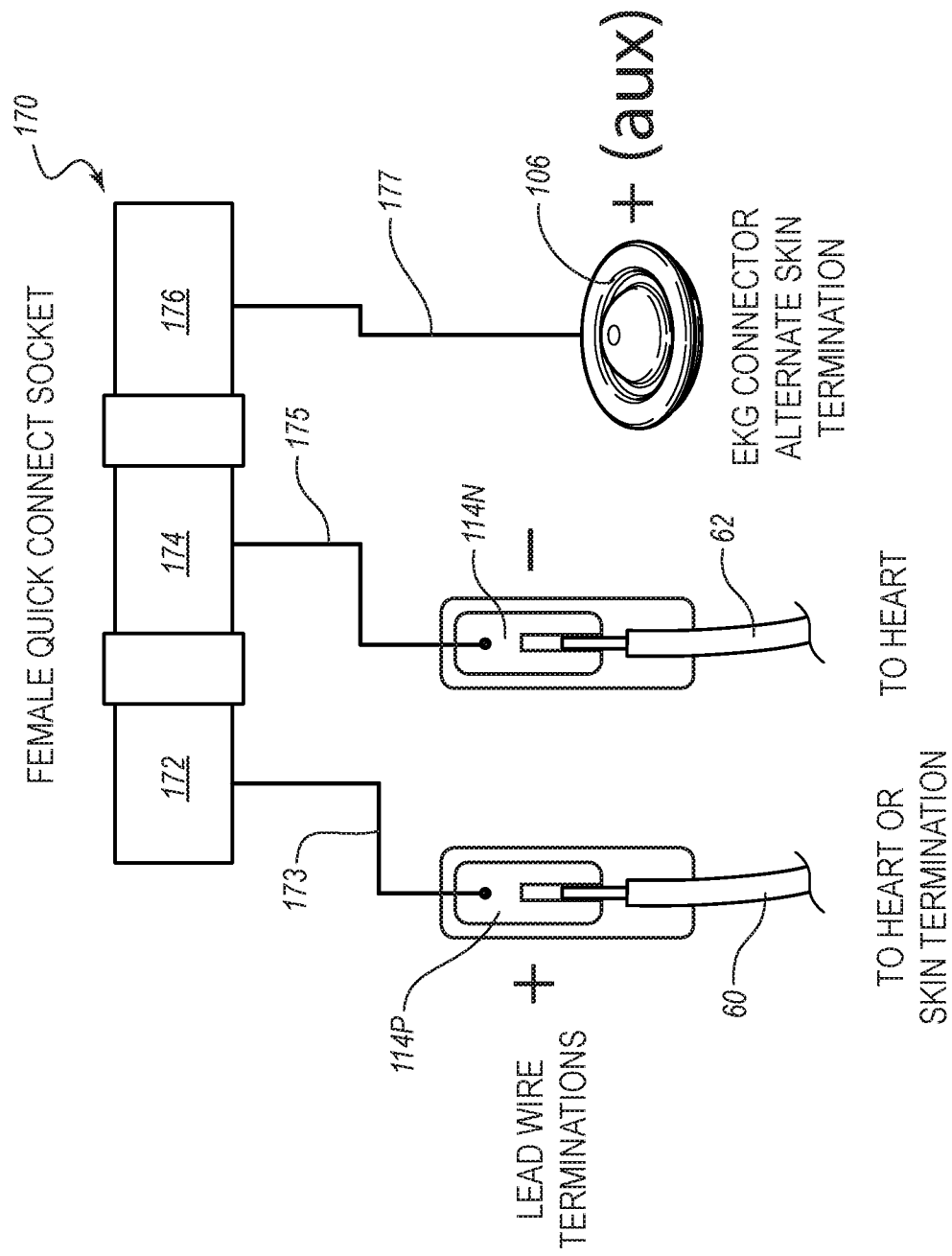
FIG. 5A is a schematic wiring diagram of a pacer wire management device.

With reference to FIGS. 4 and 5A, in some embodiments the device 100 can include a connection, electrical connection interface, or electrical port 170, such as a socket or jack. In other embodiments, no such electrical port 170 is used. The port 170 may also be referred to as a quick-connect port 170. For example, electrical connections achieved via the port 170 can be significantly quicker than can be achieved under the standard practice of inserting the tips (also referred to as terminations) of the pacer wires 60, 62 into the connection ports of an electrical cable for a pacer control unit and also tightening the tips into the connection ports. The port 170 can be attached to the spool 102 in any suitable manner. In the illustrated embodiment, the port 170 is embedded in the spool 102. The illustrated port 170 is a female socket. Other suitable port arrangements are also contemplated.

In the illustrated embodiment, the quick-connect port 170 includes three electrical contacts 172, 174, 176. As schematically illustrated in FIG. 5A, the electrical contacts 172, 174, 176 can be electrically coupled with the connectors 114P, 114N, 106, respectively, in any suitable manner. For example, the spool 102 can include electrical communication lines or electrical leads 173, 175, 177 routed through a body or other portion thereof along any suitable path to establish electrical pathways for electrical communication between the electrical contacts 172, 174, 176 and the connectors 114P, 114N, 106, respectively.

Figure 6B:
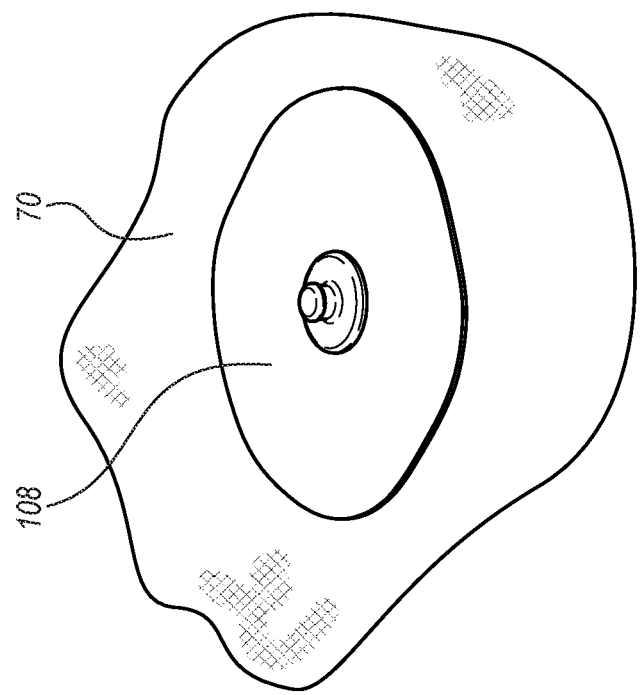
Figure 6A:
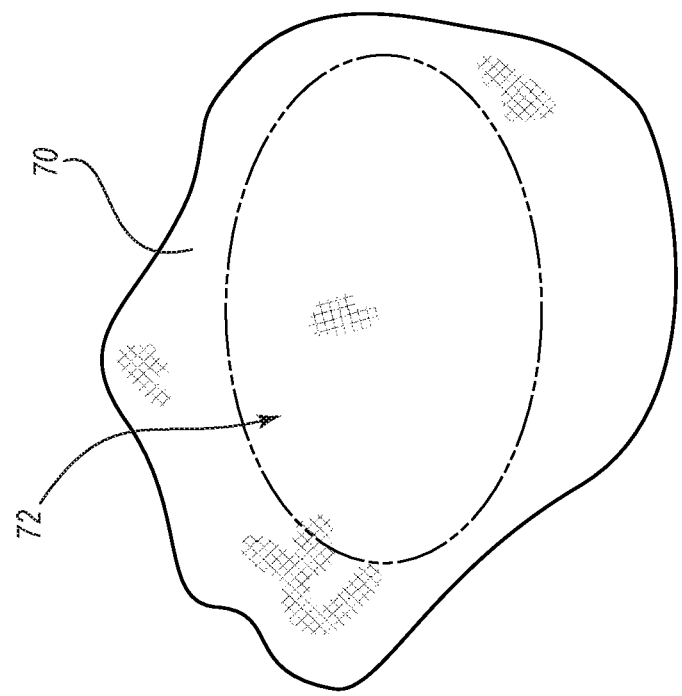
Figure 6D:
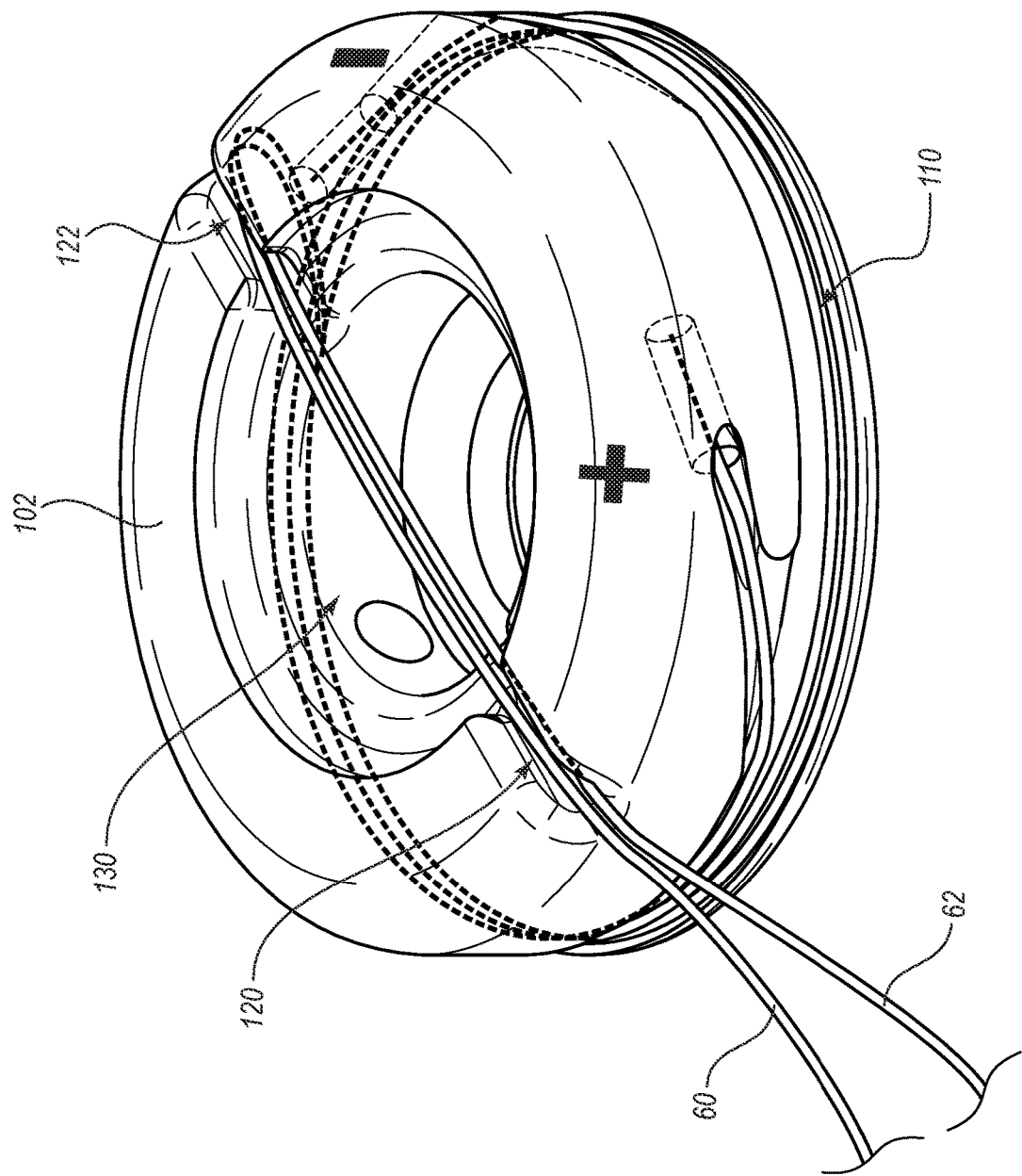
Figure 6F:
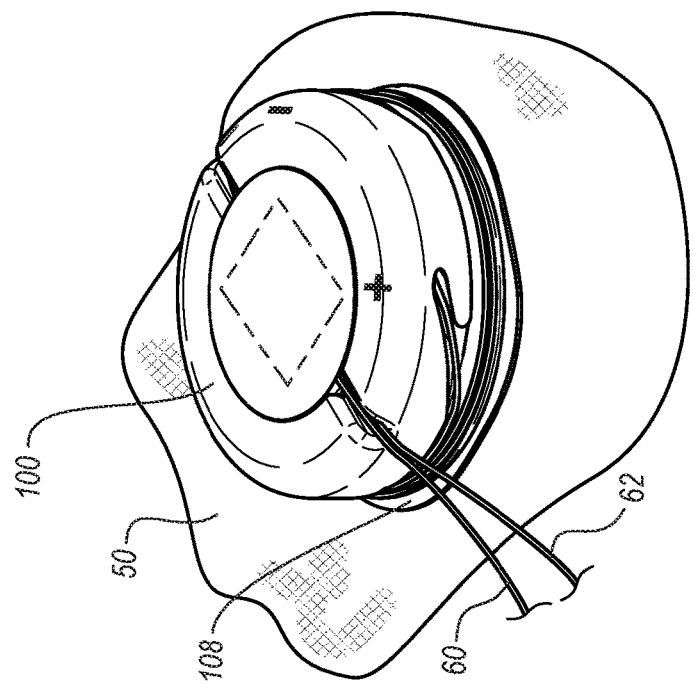
Figure 6G:
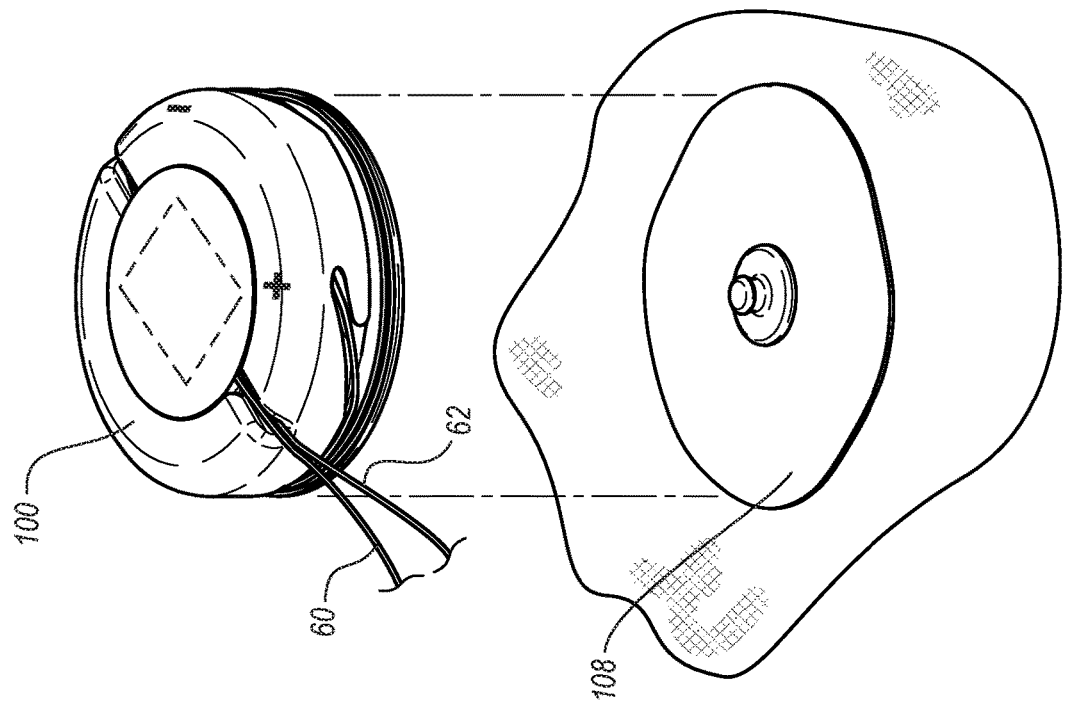
Figure 6H:
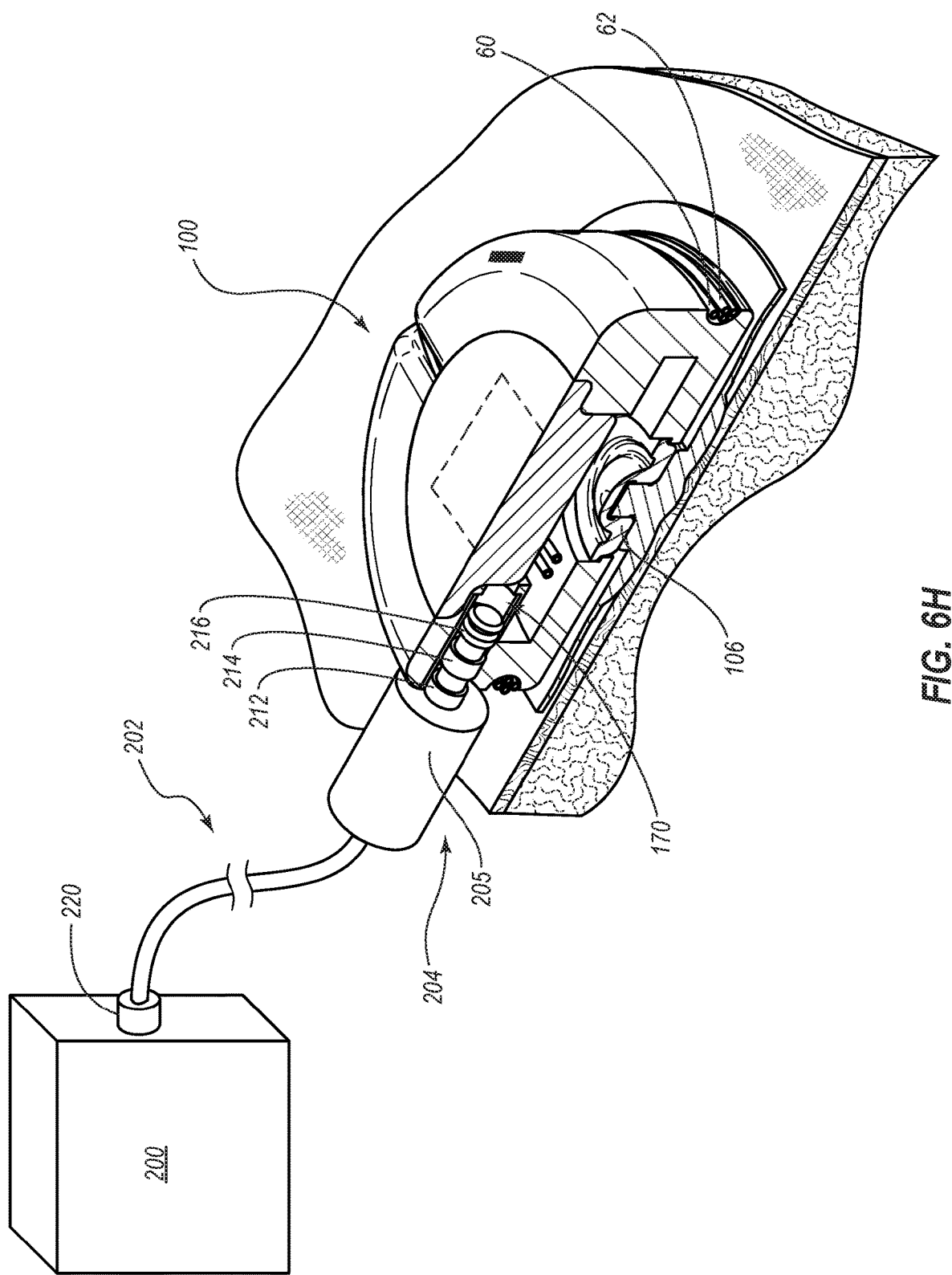

With reference to FIGS. 4, 5A, and 6H, the quick-connect port 170 can permit ready electrical coupling of a pacer control unit 200 to the pacer wires 60, 62. In some embodiments, a cable 202 is used as a communication interface between the control unit 200 and the device 100. For example, the cable 202 can either be permanently attached to the control unit 200 or can be coupled thereto via a connector 220 at one end. Another end of the cable 202 can include a connector 204 that is configured to interface with the quick-connect port 170 of the device 100. For example, in the illustrated embodiment, connector 204 comprises a male jack connector 205 that is inserted into the port 170. Such insertion establishes contact between electrical contacts 212, 214, 216 of the connector 205 and the electrical contacts 172, 174, 176 of the port 170. The control unit 200 thus can provide electrical signals to one or more of the connectors 114P, 114N, 106 via the electrical contacts 212, 214, 216.

In certain embodiments, the cable 202 indirectly connects the device 100 to the control unit 200. For example, the connector 220 can be configured to couple with a standard cable that requires insertion and clamping of exposed leads within a pair of connection ports, and the standard cable is in turn coupled to the control unit 200.

A variety of different operational modes of the control unit 200 are contemplated. For example, in some instances, the control unit 200 may provide signals to each of the electrical contacts 212, 214, 216. In other instances, the control unit 200 may only provide signals to the electrical contacts 212, 214. This operational mode corresponds with standard control units 200 that provide signals to the two implanted pacer wires 60, 62. In some of such instances, the additional contact 216 that is in electrical communication with the connector 106 lies dormant in this operational mode. For such a mode, a standard control unit 200 that may not be capable of multi-mode operation may be used.

In some instances, the control unit 200 may only provide signals to the contacts 214, 216. This operational mode corresponds with using an implanted lead 62 as the negative terminal and the connector 106 (and hence the electrode pad 108) as the positive terminal, such as a replacement for a typical skin lead. In some instances, the additional contact 212 that is in electrical communication with the connector 114P lies dormant in this operational mode.

In some instances, it is possible to switch between the two operational modes just described by using any suitable type of switch (e.g., mechanical, electrical) at one or more positions along the communication pathway. For example, the one or more switches may be incorporated into the control unit 200, the cable 202, or the device 100. For example, the one or more switches may be used to selectively activate some or all of the communication pathway that includes the electrical contacts 212, 172 and the connector 114P, while deactivating some or all of the communication pathway that includes the electrical contacts 216, 176 and the connector 106, and vice versa.

Figure 5B:
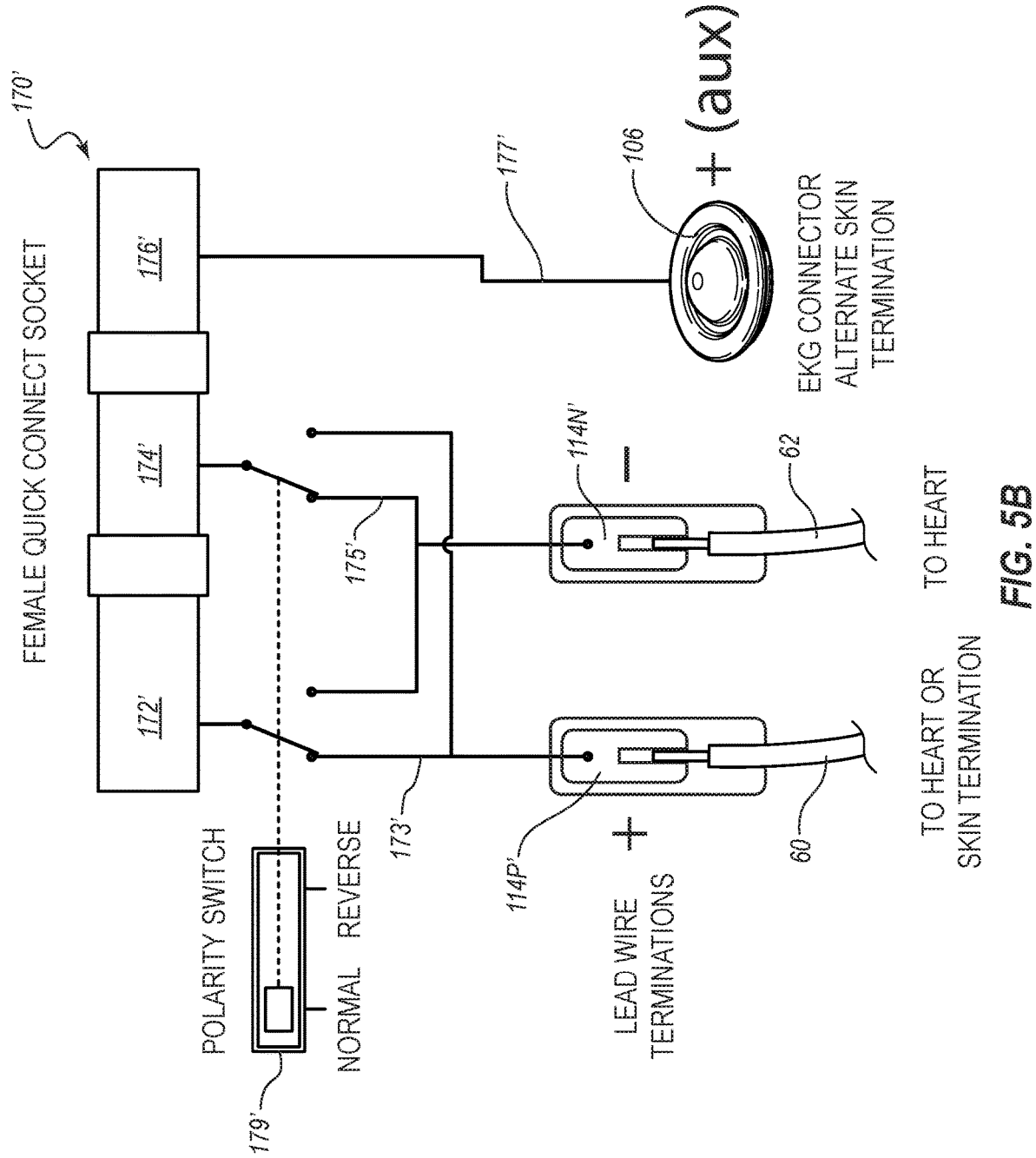
FIG. 5B is a schematic wiring diagram of another embodiment of a pacer wire management device.

In certain embodiments, the device 100 includes a polarity switch 179', such shown in FIG. 5B. As shown in FIG. 5B, the switch 179' (e.g., mechanical, electrical) can be disposed along the communication pathway. The switch 179' can also be configured to reverse the polarity of the device 100. For example, a switch 179' can be used to selectively change one or more electrical communication lines 173', 175' from a first electrical port terminal (e.g., 114P') to a second electrical port terminal (e.g., 114N'). With reference to FIG. 5B, for instance, a switch 149' can be used to change the communication pathways that extend between electrical contacts 172', 174' and the connectors 114P', 114N'. In a first position (e.g., a normal position) electrical contact 172' is electrically coupled to connector 114P' via electrical communication line 173', and electrical contact 174' is coupled to connector 114N' via electrical communication line 175'. In a second position (e.g., a reverse position) electrical contact 172' is electrically coupled to connector 114N' via electrical communication line 175', and electrical contact 174' is coupled to connector 114P' via electrical communication line 173'.

Incorporation of such a switch 179' can be advantageous in many ways. For example, use of a switch 179' can aid in instances in which the pacer wires 60, 62 are coupled with the device 100 incorrectly, or backwards. For example, in some instances a pacer wire 62 extending to the heart is connected to the positive terminal 114P' rather than the negative terminal 114N'. Use of a switch 179' can also aid in instances in which a pacer wire 60, 62 fails. For example, in some instances the pacer wire 62 connected to the negative terminal 114N' may break or otherwise fail. In such instances, it may be advantageous to switch the communication pathway from electrical contact 174' such that it extends to a second pacer wire 60. Further, a separate skin wire can be used, or the device 100 can be coupled to an electrical pad for skin termination via connector 106. For example, as shown in the illustrated embodiment, an electrical pathway in port 170' can extend from electrical contact 176' to the connector 106 along the electrical communication line 177'. Other types of switches and arrangements of switches can also be used.

FIGS. 6A-6H depict illustrative stages of an illustrative method of using the device 100. FIG. 6A depicts a stage in which a region 72 of the skin 70 of the patient is prepared for attachment of the mounting pad 108 thereto (which can include an electrode or electrode pad). Any suitable preparation method is contemplated, and may be conducted according to accepted protocols.

FIG. 6B depicts attachment of the mounting pad 108 to the region 72 of prepared skin 70. In many instances, this stage involves any suitable attachment method, and may be conducted according to accepted protocols.

FIG. 6C depicts insertion of the terminal ends of the pacer wires 60, 62 into the connectors 114P, 114N. Stated otherwise, the tips of the pacer wires 60, 62 are physically and electrically coupled to the connectors 114P, 114N.

FIG. 6D depicts a stage in which the pacer wires 60, 62 have been wrapped around the spool 102 several times while being pulled firmly into the groove 110. The wrapping may be achieved in any suitable manner, such as by rotating the spool 102 relative to the patient. Such an approach may, in some instances, introduce less twisting to the pacer wires 60, 62 than if the spool 102 is held rotationally at rest relative to the patient and the pacer wires 60, 62 are wound around the spool 102. In the depicted stage, the pacer wires 60, 62 have been wound around the spool 102 in a clockwise direction. A portion of the pacer wires 60, 62 that is closer to insertion/exit sites 80, 82 (see FIG. 1) than is the wrapped portion of the pacer wires 60, 62 is laid in the notches 122, 120 so as to span the cavity 130.

In some instances, one of the pacer wires 60, 62 may be longer than the other pacer wire 60, 62 at the stage depicted in FIG. 6C. In such instances, it may be desirable to begin the wrapping procedure by wrapping only the longer pacer wire 60, 62 into the groove 110 until the unwound portions of the pacer wires 60, 62 are substantially the same length. From that point on, both pacer wires 60, 62 may be wrapped around the spool 102 simultaneously.

FIG. 6E depicts a stage at which the cap 104 is being coupled with the spool 102. The protrusion 140 of the cap 104 will urge the portions of the pacer wires 60, 62 that span the cavity 130 downward into the cavity 130.

FIG. 6F depicts a stage at which the device 100, with the pacer wires 60, 62 secured thereto, is being coupled with the mounting pad 108. In the illustrated embodiment, the device 100 is forced downward onto the mounting pad 108 to achieve a snap-fit engagement. Other types of engagements can also be used.

FIG. 6G depicts a stage at which the device 100, with the pacer wires 60, 62 secured thereto, has been coupled with the mounting pad 108. In turn, the device 100 has been coupled to the patient 50. As can be appreciated, the distal ends or portions of the pacer wires 60, 62 can be disposed within the patient (e.g., coupled to the heart) prior to wrapping the pacer wires 60, 62 around the device 100.

FIG. 6H depicts a stage at which the device 100, now coupled with both the pacer wires 60, 62 and the patient 50, has been electrically coupled with the control unit 200. Operation of the control unit 200 and the device 100 in this coupled state has been discussed previously.

FIG. 7 is a perspective view of another embodiment of a pacer wire management device 300 that resembles the device 100 in many respects. Accordingly, like features are designated with like reference numerals, with the leading digits incremented to "3." Relevant disclosure set forth above regarding similarly identified features thus may not be repeated hereafter. Moreover, specific features of the device 300 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the device 300. Any suitable combination of the features, and variations of the same, described with respect to the device 100 can be employed with the device 300, and vice versa. This pattern of disclosure applies equally to further embodiments depicted in subsequent figures and described hereafter, wherein the leading digits may be further incremented.

As shown in FIG. 7, in some embodiments the device 300 includes a cap 304 that is secured or otherwise tethered to the spool 302 using a coupling member 307. In certain embodiments, the coupling member 307 comprises a tether. In other embodiments, the coupling member 307 comprises a hinge or hinge-like structure. Other types of coupling members 307 can also be used.

As shown in the illustrated embodiment, the coupling member 307 can be configured to couple the cap 304 to the spool 302 such that the cap 304 remains coupled to the spool 302 when the connection interfaces between the cap 304 and spool 302 are disengaged. After the pacer wires 60, 62 have been appropriately wrapped and/or positioned, the cap 304 can be further coupled or engaged with the spool 302 in a position that at least partially retains the pacer wires 60, 62 (such as the position depicted in FIG. 6H). For example, a protrusion on the cap 304 can be inserted into a recess or cavity of the spool 302 to aid in retaining the pacer wires 60, 62.

FIGS. 8A and 8B depict perspective views of another embodiment of a pacer wire management device 400. As shown in FIGS. 8A and 8B, the device 400 comprises a spool 402 and a cap 404 that are configured to retain one or more pacer wires 60, 62. In the illustrated embodiment, the cap 404 comprises a cover that can be disposed at least partially over the spool 402. The cap 404 further comprises a channel or port 409 through which the pacer wires 60, 62 can extend. In some embodiments, the cap 404 is coupled or secured to the spool 402 using a coupling member 407. In other embodiments, no coupling member 407 is used.

As disclosed herein, one or more pacer wires 60, 62 can be wrapped around the spool 402. After the pacer wires 60, 62 have been appropriately wrapped and/or positioned, the cap 402 can be coupled with and at least partially disposed over the spool 402. As shown in the illustrated embodiment of FIG. 8B, the cap 404 can cover or otherwise enclose a portion of the spool 402. In particular embodiments, the cap 404 covers the channel or groove into which the pacer wires 60, 62 are wound. For example, the cap 404 can cover at least a portion, or an entirety, of the channel or groove into which the pacer wires 60, 62 are wound. In such instances, the cap 404 can also at least partially, or completely, cover or enclose the portions of the pacer wires 60, 62 that are wound around the spool 402 and disposed in the channel or groove. Such an arrangement can aid in keeping the pacer wires 60, 62 in a wrapped position within the channel or groove. Stated otherwise, the cap 404 can help prevent the pacer wires 60, 62 from unwinding or unspooling. Such an arrangement may also inhibit inadvertent snagging of the wrapped portion of the pacer wires 60, 62.

In certain embodiments, the cap 404 further comprises a protrusion 440, similar to the protrusion of the cap 104 discussed in relation to FIGS. 1-4. When the cap 404 is coupled to the spool 402, the protrusion can be received within a recess or cavity 430 of the spool 402 to aid in retaining the pacer wires 60, 62. Additionally, it will be appreciated that the cap 404 and spool 402 can include various connection interfaces, such as the connection interfaces 132, 142 discussed in relation to the cap 104 of FIGS. 1-4. Other types of connection interfaces can also be used to couple the cap 404 and spool 402 to one another, such as a connection interface disposed on the outer perimeter of the spool 402 and/or a connection interface disposed on an inner perimeter or inner surface of the cap 404.

Figure 9:
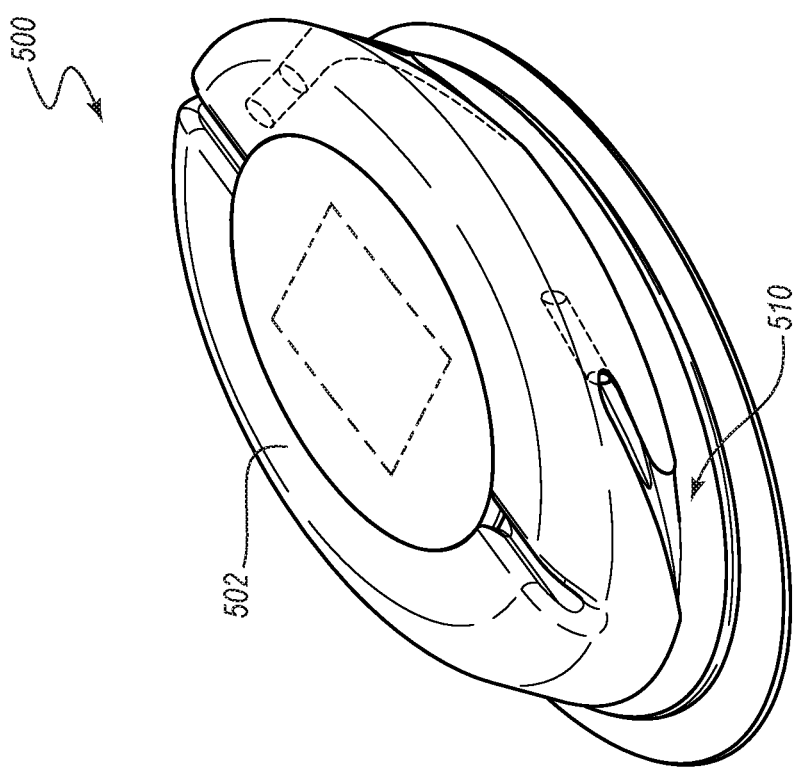
FIG. 9 is a perspective view of another embodiment of a pacer wire management device.

FIG. 9 is a perspective view of yet another embodiment of a pacer wire management device 500. As shown in FIG. 9, the shape of the device 500 can vary as desired. For example, in the illustrated embodiment, the device 500 is elongated or substantially oval in shape. Stated another way, a perimeter that extends around the device 500 (or groove 510 of the device 500) is substantially oval in shape rather than circular (as is shown in the device of FIGS. 1-4).

The size of the device 500 can also vary as desired. For example, the perimeter around the device 500 can be made larger or smaller. The thickness of the device 500 can also be increased (thicker) or decreased (thinner) as desired. It will thus be appreciated that the size and/or shape of the device 500 can be varied.

Figure 10:
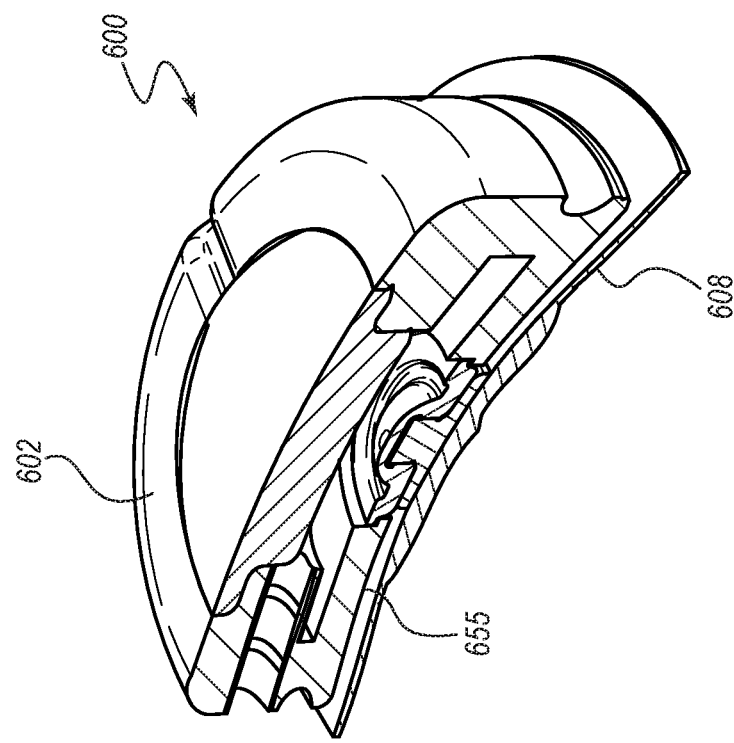
FIG. 10 is a cross-sectional perspective view of another embodiment of a pacer wire management device.

FIG. 10 is a cross-sectional perspective view of a pacer wire management device 600 in accordance with another embodiment. In FIG. 10, a bottom surface 655 of the spool 602 is curved or arcuate rather than flat. Such an arrangement can aid in fitting the device 600 onto a portion of patient's body (e.g., such as fitting the device 600 onto a contour of a patient's belly). Such an arrangement can also aid in preventing the device 600 from rotating once it is coupled to a mounting pad 608 or otherwise disposed on a surface of the patient's skin. Other shapes and/or configurations can also be used.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub routines or only a portion of a method illustrated in the drawings, such as a small subset of a step, may be a separate method. Stated otherwise, some additional methods may include only a portion of the steps shown in a more detailed method.

References to approximations are made throughout this specification, such as by use of the terms "substantially," "about" or "approximately." For each such reference, it is to be understood that, in some embodiments, the value, feature, or characteristic may be specified without approximation. For example, where qualifiers such as "substantially," "about" or "approximately" are used, these terms include within their scope the qualified words in the absence of their qualifiers.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Embodiments of the invention in which an exclusive property or privilege is claimed are defined as follows.

The invention claimed is:

1. A medical wire management device, comprising:
    a spool having:
        a front face;
        a back face opposite the front face; and
        a groove disposed between the front face and the back face and extending about a perimeter of the spool such that one or more wires may be wrapped there about;
    a first electrical connector attached to the spool near the groove, the first connector comprising an electrical connector that is configured to be electrically coupled with a wire;
    a second electrical connector attached to the spool spaced from the first electrical connector, not directly electrically coupled thereto, and configured to be electrically coupled with a wire;
    a physical connector disposed on the back face of the spool and configured to selectively physically couple the spool to a mounting pad; and
    an electrical port attached to the spool and including:
        a first electrical contact, and
        a second electrical contact electrically separate from the first electrical contact, wherein the first electrical contact is electrically coupled to the first electrical connector and the second electrical contact is electrically coupled to the second electrical connector.

2. The device of claim 1, further comprising a recessed channel through the spool near the first electrical connector, the recessed channel being in communication with the groove.

3. The device of claim 2, wherein the recessed channel defines an acute angle relative to the groove.

4. The device of claim 1, further comprising a cap shaped to cover and enclose the spool, the cap being selectably coupleable over the spool.

5. The device of claim 1, wherein the physical connector is also in electrical communication with the port.

6. The device of claim 5, wherein the physical connector is in electrical communication with the first electrical connector but not in electrical communication with the second electrical connector.

7. The device of claim 1, wherein the electrical port is a female socket extending into the spool through a side Lace of the spool that is adjacent to the front face of the spool.

8. The device of claim 1, further comprising one or more indicia to specify the polarity of the first electrical connector.

9. The device of claim 1, further comprising:
    a polarity switch functionally coupled to the electrical port such that when switched the polarity switch swaps electrical connectivity of the first electrical contact and the second electrical contact with respect to each of the first electrical connector and the second electrical connector.

10. A medical wire management kit, comprising:
    the medical wire management device of claim 1; and
    a mounting pad having a connector button protruding therefrom to which the physical connector selectably connects.

11. The kit of claim 10, further comprising a cap configured to couple with the spool.

12. The kit of claim 10, further comprising a cable having a connector jack that couples to the electrical port.

* * * * *